United States Patent [19]

Kröck et al.

[11] Patent Number: 4,521,341
[45] Date of Patent: Jun. 4, 1985

[54] PROCESS FOR THE PREPARATION OF 1,4-DIAMINO-ANTHRAQUINONE-2-SULPHONIC ACID

[75] Inventors: Friedrich W. Kröck, Cologne; Rütger Neoff, Leverkusen, both of Fed. Rep. of Germany

[73] Assignee: Bayer Aktiengesellschaft, Leverkusen, Fed. Rep. of Germany

[21] Appl. No.: 590,133

[22] Filed: Mar. 16, 1984

Related U.S. Application Data

[63] Continuation of Ser. No. 313,025, Oct. 19, 1981, abandoned.

[30] Foreign Application Priority Data

Nov. 8, 1980 [DE] Fed. Rep. of Germany ....... 3042241

[51] Int. Cl.³ .......................................... C07C 143/665
[52] U.S. Cl. .................................................... 260/371
[58] Field of Search ......................................... 260/371

[56] References Cited

U.S. PATENT DOCUMENTS

| | | | |
|---|---|---|---|
| 3,234,242 | 2/1966 | Basel et al. | 260/367 |
| 3,507,850 | 4/1979 | Cohen et al. | 260/371 |
| 4,042,605 | 8/1977 | Hartwig | 260/369 |
| 4,294,769 | 10/1981 | Krock et al. | 260/378 |

FOREIGN PATENT DOCUMENTS

| | | | |
|---|---|---|---|
| 0023645 | 7/1980 | European Pat. Off. | |
| 0034257 | 1/1981 | European Pat. Off. | |
| 1142174 | 1/1963 | Fed. Rep. of Germany | 260/371 |
| 1155786 | 10/1963 | Fed. Rep. of Germany | 260/371 |
| 1273712 | 9/1961 | France | 260/371 |

OTHER PUBLICATIONS

E. de Barry Barnett, *Anthracene and Anthraquinone,* 1921, Van Nostrand Co., New York, N.Y., p. 196.

*Primary Examiner*—Glennon H. Hollrah
*Assistant Examiner*—Raymond Covington
*Attorney, Agent, or Firm*—Sprung, Horn, Kramer & Woods

[57] ABSTRACT

1,4-Diamino-anthraquinone-2-sulphonic acid is obtained in a simple manner, in good yield and good purity, by reacting 1-amino-4-bromo-anthraquinone-2-sulphonic acid with ammonia in water in the presence of copper catalysts at an elevated temperature, under a partial pressure of ammonia of at least 5 bar.

8 Claims, No Drawings

PROCESS FOR THE PREPARATION OF 1,4-DIAMINO-ANTHRAQUINONE-2-SULPHONIC ACID

This is a continuation of application Ser. No. 313,025, filed Oct. 19, 1981, now abandoned.

The invention relates to a process for the preparation of 1,4-diamino-anthraquinone-2-sulphonic acid

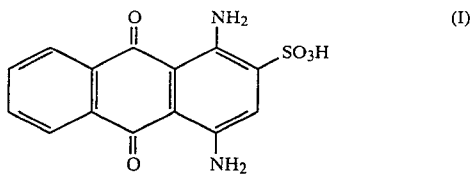

or of its salts by reacting 1-amino-4-bromo-anthraquinone-2-sulphonic acid, or its salts, with ammonia.

It is already known that 1,4-diamino-anthraquinone-2-sulphonic acid or its salts can be prepared in good yield and good purity by reacting 1-amino-4-bromoanthraquinone-2-sulphonic acid or its salts in liquid ammonia at 60°–100° C., under a pressure sufficient to ensure that liquid ammonia is still present, in the presence of copper or copper salts (German Patent Specification No. 1,142,174) or of copper oxide (German Patent Specification No. 1,155,786). This process has the disadvantage that it is carried out with liquid ammonia, without an additional solvent, at near the critical temperature of ammonia. In this process, especially when carried out on an industrial scale, severe complications can arise through product deposition on the vessel walls, and through overheating.

It is furthermore known that 1-amino-4-bromoanthraquinone-2-sulphonic acid can be converted, by heating with ammonia in the presence of copper, to the compound shown in the title (German Patent Specification No. 263,395). There are no data concerning the reaction conditions and yields.

Finally, U.S. Pat. No. 3,507,850 (Example 83, in combination with Example 80) has disclosed reacting 1-amino-4-bromo-anthraquinone-2-sulphonic acid with aqueous amine solutions or aqueous ammonia at 80° C., in the presence of copper-(II) sulphate, to give the corresponding 1,4-diamino compound. Here again, data concerning yield, purity and the like are lacking.

However, it has been found, in repeating these only incompletely described reactions in the temperature range of 20°–100° C., using 25% strength aqueous ammonia and various copper salt catalysts, that the reaction takes place only very incompletely. In addition to a large amount of unchanged starting material, the 4-hydroxy derivative, the 1,1'-dianthraquinonyl derivative formed by "Ullmann condensation", and a series of other nonidentified by-products were obtained, and these are difficult to separate from the desired 1,4-diamino derivative.

These observations, furthermore, substantially agree with those made by others (cf. German Patent Specification No. 1,142,174, top of column 1).

It has now been found that 1,4-diamino-anthraquinone-2-sulphonic acid and its salts, which are important dyestuff intermediates, are obtained in a simple manner, in good yield and good purity, if the reaction of 1-amino-4-bromo-anthraquinone-2-sulphonic acid, or of its salts, with ammonia is carried out in water, in the presence of copper, copper oxides and/or copper salts, at an elevated temperature and if appropriate in the presence of acid-binding agents, under a partial pressure of ammonia of at least 5 bar.

It must be described as extremely suprising that the reaction of 1-amino-4-bromo-anthraquinone-2-sulphonic acid with ammonia in water under the reaction conditions employed, under pressure, should take place so uniformly and smoothly to give 1,4-diamino-anthraquinone-2-sulphonic acid, without the formation of significant amounts of 1-amino-4-hydroxy-anthraquinone-2-sulphonic acid, as reported in German Patent Specification No. 1,142,174.

1-Amino-4-bromo-anthraquinone-2-sulphonic acid and its salts, especially the sodium salt, are largescale industrial products. The amount of solvent, water or aqueous ammonia can vary within a substantial range and essentially depends on the solubility of the starting material and of the end product. What is required under all circumstances is that an easily stirrable system should form, in which the starting material and the end product are preferably completely dissolved. In general, this requires 0.5 to 5 kg of water or aqueous ammonia per mol of 1-amino-4-bromoanthraquinone-2-sulphonic acid. By aqueous ammonia there is preferably understood a cold saturated solution of ammonia and water, that is to say an aqueous ammonia solution of about 25 to 30 percent strength by weight.

The reaction is carried out at 40° to 120° C., or, in a preferred embodiment, at 60° to 100° C., under a partial pressure of ammonia of 5 to 30 bar, preferably of 10 to 20 bar.

The amount of ammonia which is required per mol of 1-amino-4-bromo-anthraquinone-2-sulphonic acid to be converted can be between 100 and 2,000 g; an amount of 500 to 1,500 g is preferred. The amount is so chosen that, at the reaction temperature, the required pressure results. Under practical conditions, the procedure followed is that the 1-amino-4-bromo-anthraquinone-2-sulphonic acid, or one of its salts, water or the aqueous ammonia solution, and the copper catalyst, with or without the acid-binding agent, are introduced into an autoclave, the autoclave is closed and, where necessary, an appropriate proportion of the ammonia is forced into the autoclave, as liquid or gas, so that the pressure, on heating to the reaction temperature, does not exceed the prescribed limit. Further ammonia is then introduced so that the prescribed ammonia pressure is maintained over the entire reaction time.

Suitable copper catalysts are finely divided metallic copper (so-called copper bronze), copper(I) oxide, copper(II) oxide and copper salts, for example copper carbonate, basic copper carbonate, copper acetate, basic copper acetate, copper formate, copper(I) chloride, copper(II) chloride, copper(II) sulphate, copper(I) bromide, copper(II) bromide and others, as well as complex compounds of copper and mixtures of copper or copper salts with complexing agents, for example copper tetrammine sulphate, copper/potassium sodium tartrate and others. The copper or copper compounds are employed in catalytic amounts, that is to say in amounts of 0.1 to 10 g per mol of 1-amino-4-bromo-anthraquinone-2-sulphonic acid to be reacted.

As suitable acid-binding agents it is optionally possible to add, in particular, sodium carbonate, sodium bicarbonate, potassium carbonate, sodium acetate or potassium acetate, the amount of acid-binding agent added preferably being equivalent to the amount of HBr to be eliminated.

The reaction time is about 1 to 10 hours. Thereafter, excess ammonia is distilled off and, if necessary, to a large extent removed by applying a slight vacuum.

The reaction product 1,4-diamino-anthraquinone-2-sulphonic acid can—after checking for completeness of the reaction, for example by thin layer chromatography—be directly reacted further in the solution, for example be reacted with cyanides, in a manner known in principle, to give 1,4-diamino-2,3-dicyano-anthraquinone (compare German Patent Specification No. 1,108,704, corresponding to British Patent Specification No. 901,059); alternatively, the reaction product is isolated in a conventional manner by precipitation through acidification, or by salting out.

EXAMPLE 1

A solution of 1.2 g of copper sulphate pentahydrate in 400 ccs of 25 percent strength aqueous ammonia solution is introduced into an 0.7 l autoclave and 87.4 g of 87.5 percent strength 1-amino-4-bromo-anthraquinone-2-sulphonic acid (as sodium salt; strength calculated as free acid) are introduced, with stirring. The autoclave is sealed and heated to 80° C., and sufficient gaseous or liquid ammonia is then forced in to reach a pressure of 15 bar. The mixture is heated at 80° C. for 10 hours, with stirring, additional ammonia being introduced whenever the pressure drops by more than 0.1 bar. In total, about 270 ccs of liquid ammonia (measured under pressure at room temperature) are forced in. The autoclave is then cooled, the pressure released and excess ammonia removed by applying a vacuum. The reaction mixture is then freed from small amounts of insoluble constituents by filtration. A thin layer chromatogram shows that the reaction mixture no longer contains any 1-amino-4-bromo-anthraquinone-2-sulphonic acid. Determination by ultraviolet and visual photometry shows that the solution contains 57.4 g of 1,4-diamino-anthraquinone-2-sulphonic acid, corresponding to a yield of 90.2% of theory. The reaction solution is made up to about 1 l and is acidified with concentrated sulphuric acid, so that the 1,4-diamino-anthraquinone-2-sulphonic acid crystallises out as the sulphate, and the exudate of the suspension on filter paper is virtually colourless. The reddish brown sulphate is then filtered off and washed carefully with water until the initially almost colourless filtrate assumes a pale violet colour. After drying at 60° C., 60.3 g of a product are obtained; according to analysis, this consists of 92.2% of 1,4-diamino-anthraquinone-2-sulphonic acid and 0.9% of 1-amino-4-hydroxy-anthraquinone-2-sulphonic acid, and no longer contains anyl-amino-4-bromo-anthraquinone-2-sulphonic acid. This corresponds to a yield of pure material, as isolated product, of 87.4%, which agrees well with the yield of 90.2% determined by ultraviolet/visual photometry.

EXAMPLE 2

The charge described in Example 1 is employed, the autoclave is sealed, 180 ccs of liquid ammonia (measured at room temperature under pressure) are forced in, the mixture is heated to 80° C. and a pressure of 20 bar is maintained by adding further ammonia (about 120 ccs of liquid ammonia being required for this purpose); after releasing the pressure and applying a vacuum, as described in Example 1, a solution is obtained which, after dilution with water, precipitation with about 100 ccs of concentrated sulphuric acid, filtering off of the product and washing it as in Example 1, gives 64.5 g of 1,4-diamino-anthraquinone-2-sulphonic acid as a 94.5% pure product, which contains no 1-amino-4-bromo-anthraquinone-2-sulphonic acid and only 0.2% of 1-amino-4-hydroxy-anthraquinone-2-sulphonic acid. This corresponds to a yield of pure material of 95.8%.

EXAMPLE 3

The charge described in Example 1 is employed, the autoclave is sealed, 170 ccs of liquid ammonia (measured at room temperature under pressure) are forced in, the mixture is heated to 80° C. and a pressure of 15 bar is maintained by adding further ammonia (about 120 ccs of liquid ammonia being required for this purpose); after releasing the pressure and applying a vacuum, as described in Example 1, a solution is obtained, which is made up to 1 l with water, and filtered. After acidifying the filtrate with about 100 ccs of concentrated sulphuric acid, filtering off the product and washing it as before, 67.8 g of 1,4-diamino-anthraquinone-2-sulphonic acid are obtained as a 91.6% pure product which contains no 1-amino-4-bromo-anthraquinone-2-sulphonic acid and only 0.3% of 1-amino-4-hydroxy-anthraquinone-2-sulphonic acid. This corresponds to a yield of pure material of 97.6%.

EXAMPLE 4

The charge described in Example 1 is employed, the autoclave is sealed, 100 ccs of liquid ammonia (measured at room temperature under pressure) are forced in, the mixture is heated to 80° C. and a pressure of 10 bar is maintained by adding further ammonia (about 102 ccs of liquid ammonia being required for this purpose); after releasing the pressure and applying a vacuum, as described in Example 1, a solution is obtained which, according to ultraviolet/visual photometric determination, contains 58.7 g of 1,4-diamino-anthraquinone-2-sulphonic acid. This corresponds to a yield of pure material of 92.2%.

The solution obtained is used, as described in Example 7, for the preparation of 1,4-diamino-2,3-dicyanoanthraquinone, giving 55.7 g of a dark blue powder which, according to analysis, contains 79.4% of 1,4-diamino-2,3-dicyano-anthraquinone and 10.5% of 1,4-diamino-2-cyano-anthraquinone, corresponding to a yield of pure 1,4-diamino-2,3-dicyano-anthraquinone of 76.7%, relative to 1-amino-4-bromo-anthraquinone-2-sulphonic acid.

EXAMPLE 5

A solution of 6 g of copper sulfate pentahydrate in 2 l of 25 percent aqueous ammonia solution is introduced into a 3 l V4A stainless steel autoclave and 437 g of 87.5 percent strength 1-amino-4-bromo-anthraquinone-2-sulphonic acid (as Na salt; strength calculated as free acid) are introduced, with stirring. The autoclave is sealed, 500 ccs of gaseous or liquid ammonia (measured at room temperature under pressure) are forced in and the reaction mixture is heated to 80° C., with stirring. This generates a pressure of 7.8 bar, which is increased to 12 bar by further addition of liquid ammonia. The mixture is kept at 80° C. for 5 hours, with stirring, further ammonia being introduced whenever the pressure drops below 12 bar. In total, an additional 282 ccs of liquid ammonia (measured at room temperature under pressure) are forced in. After cooling, releasing the pressure, and stripping off the excess ammonia by applying a vacuum, a solution is obtained, which is filtered and made up to 3,250 g with water. Ultraviolet/visual photometry shows that the solution contains 275.5 g of 1,4-diamino-anthraquinone-2-sulphonic acid; this corresponds to a reaction yield of 86.6%. The starting product is no longer detectable in this solution by thin layer chromatography. The solution obtained is used, in Example 10, for the preparation of 1,4-diamino-2,3-dicyano-anthraquinone.

If the above batch is repeated but additionally 53 g of anhydrous sodium carbonate are dissolved in the 25 percent aqueous ammonia solution, a solution is obtained which according to ultraviolet/visual photometry contains 283.7 g of 1,4-diamino-anthraquinone-2-sulphonic acid, corresponding to a reaction yield of 89.2%. 1-Amino-4-bromo-anthraquinone-b 2-sulphonic acid is no longer detectable by thin layer chromatography. Similar results are also obtained if instead of sodium carbonate 69 g of potassium carbonate, 84 g of sodium bicarbonate, 82 g of sodium acetate or 98 g of potassium acetate are used.

EXAMPLE 6

The charge described in Example 1 is employed, except that in place of copper sulphate 1.0 g of copper bronze is used; the autoclave is sealed and heated to 80° C. with stirring, and sufficient liquid ammonia is forced in that during the entire reaction a pressure of 12 bar is maintained, which requires, in total, about 240 ccs of liquid ammonia (measured at room temperature under pressure). After a reaction time of 5 hours, followed by working up as in Example 1, an aqueous solution of 1,4-diamino-anthraquinone-2-sulphonic acid is obtained, which, according to a thin layer chromatogram, no longer contains any starting material.

The solution obtained is used in Example 11 for the preparation of 1,4-diamino-2,3-dicyano-anthraquinone.

Comparably good results are also obtained if in place of copper bronze 1.2 g of copper(I) chloride, which has, if desired, first been dissolved in 12 g of saturated sodium chloride solution plus a few drops of concentrated hydrochloric acid, 1.0 g of copper(I) oxide, 1.2 g of copper(II) oxide, 1.2 g of copper acetate, 1.2 g of basic copper acetate, 1.2 g of copper carbonate, 1.2 g of basic copper carbonate or 1.5 g of copper(I) bromide are used as the catalyst.

EXAMPLE 7

490 g of a reaction solution according to Example 1, corresponding to 28 g of pure 1,4-diamino-anthraquinone-2-sulphonic acid (determined by ultraviolet/visual photometry), 6.4 g of crystalline sodium acetate ($+3H_2O$), 36 g of sodium cyanide, 0.6 g of ammonium vanadate and 1,040 ccs of water are heated to 90° C. in the course of one hour and stirred at 90° to 95° C. for 4 hours. In the course thereof, a steady stream of air at the rate of 5.6 l per hour is passed through the mixture. The 1,4-diamino-anthraquinone-2,3-dinitrile formed separates out in the form of fine crystal needles. It is filtered off hot, washed with hot water and dried. The yield is 24.8 g. According to analysis, the product consists of 80.6% of 1,4-diamino-2,3-dicyano-anthraquinone and 11.2% of 1,4-diamino-2-cyano-anthraquinone; this corresponds to a yield of 78.8% of pure 1,4-diamino-2,3-dicyano-anthraquinone, relative to 1,4-diamino-anthraquinone-2-sulphonic acid employed.

EXAMPLE 8

A solution of 45.5 g of sodium m-nitrobenzenesulphonate, in 481 g of water is run slowly, in the following manner; into a mixture, warmed to 45° C., of 1,000 g of a reaction solution according to Example 1, corresponding to 58.5 g of pure 1,4-diamino-anthraquinone-2-sulphonic acid (determined by ultraviolet/visual photometry), 13 g of sodium carbonate, 78 g of sodium cyanide and 2,300 ccs of water: 188.5 g of the solution are introduced into the mixture in the course of the first hour, 182 g in the course of the second hour, 97.5 g in the course of the third hour and 58.5 g in the course of the fourth hour, and stirring is then continued for 30 minutes. Whilst doing so, the reaction mixture is heated to 90° C. in the course of 30 minutes and kept at this temperature for 4 hours. The reaction product is then filtered off hot, washed with hot water until free from acid, and dried. 46.3 g of blue-black crystals are obtained, containing, according to analysis, 78.8% of 1,4-diamino-2,3-dicyano-anthraquinone and 14.5% of 1,4-diamino-2-cyano-anthraquinone. This corresponds to a yield of 68.8% of pure 1,4-diamino-2,3-dicyano-anthraquinone, relative to 1,4-diamino-anthraquinone-2-sulphonic acid employed.

EXAMPLE 9

A solution of 37 g of 94.5 percent strength 1,4-diamino-anthraquinone-2-sulphonic acid from Example 2, 8 g of crystalline sodium acetate, 45 g of sodium cyanide and 0.75 g of sodium vanadate in 1,900 ccs of water is heated to 90° C. in the course of 1 hour, whilst passing a steady stream of air at about 7 l/hour through the solution, and is then left at the same temperature for 4 hours, whilst continuing the stirring and passage of air. The product is then filtered off, washed with hot water and dried. 31.1 g of a dark blue powder are obtained, containing, according to analysis, 80.6% of 1,4-diamino-2,3-dicyano-anthraquinone and 11.2% of 1,4-diamino-2-cyano-anthraquinone, corresponding to a yield of 79.1% of pure material, relative to 1,4-diamino-anthraquinone-2-sulphonic acid employed.

EXAMPLE 10

650 g of the reaction solution from Example 5, corresponding to 55.1 g of 1,4-diamino-anthraquinone-2-sulphonic acid (determined by ultraviolet/visual photometry, and corresponding to 76.4 g of 100 percent strength 1-amino-4-bromo-anthraquinone-2-sulphonic acid employed), 71 g of sodium cyanide, 1.2 g of sodium vanadate and 2,950 ccs of water are heated to 90° C. for 11 hours, with stirring, and whilst passing a steady stream of air, at the rate of about 1 l/hour, through the reaction mixture. The product is then filtered off hot, washed with hot water and dried. Yield: 54.6 g of a dark blue powder which, according to analysis, consists of 73.4% of 1,4-diamino-2,3-dicyano-anthraquinone and 8.8% of 1,4-diamino-2-cyano-anthraquinone. The yield of pure material, relative to 1-amino-4-bromo-anthraquinone-2-sulphonic acid employed, is accordingly 69.5%, corresponding to 80.3% relative to 1,4-diamino-anthraquinone-2-sulphonic acid.

EXAMPLE 11

The preceding charge (Example 10) is used again, but employing the whole of the reaction solution from Example 6, diluted with 2 l of water. 53.5 g of a dark blue powder are obtained, consisting, according to analysis, of 76.2% of 1,4-diamino-2,3-dicyano-anthraquinone and 11.1% of 1,4-diamino-2-cyano-anthraquinone. The yield of pure material, relative to 1-amino-4-bromo-anthraquinone-2-sulphonic acid employed, is accordingly 70.7%.

We claim:

1. Process for the preparation of 1,4-diamino-anthraquinone-2-sulphonic acid and its salts by reacting 1-amino-4-bromo-anthraquinone-2-sulphonic acid, or its salts, with aqueous ammonia solution at an elevated temperature in the presence of copper catalysts and, if appropriate, in the presence of acid-binding agents, characterised in that the reaction is carried out under a partial pressure of ammonia of at least 5 bar.

2. Process for the preparation of 1,4-diamino-anthraquinone-2-sulphonic acid and its salts, according to claim 1, characterised in that the reaction is carried out under an ammonia partial pressure of at least 10 bar.

3. Process for the preparation of 1,4-diamino-anthraquinone-2-sulphonic acid and its salts, according to claim 1, characterised in that the reaction is carried out at 40° to 120° C.

4. Process for the preparation of 1,4-diamino-anthraquinone-2-sulphonic acid and its salts, according to claim 1, characterised in that the reaction is carried out at 60° to 100° C.

5. Process for the preparation of 1,4-diamino-anthraquinone-2-sulphonic acid and its salts, according to claim 1, characterised in that the copper catalysts used are copper, copper oxides, copper salts, complex compounds of copper and/or mixtures of copper or copper salts with complex-forming agents.

6. Process for the preparation of 1,4-diamino-anthraquinone-2-sulphonic acid and its salts, according to claim 1, characterised in that the copper catalysts used are finely divided copper (copper bronze), copper(I) oxide, copper(II) oxide, copper(II) sulphate, copper(I) chloride, copper(II) chloride, copper(II) acetate, basic copper acetate, copper carbonate, basic copper carbonate, copper(II) bromide, copper(I) bromide or copper tetrammine sulphate.

7. Process for the preparation of 1,4-diamino-anthraquinone-2-sulphonic acid and its salts, according to claim 1, characterised in that the copper catalysts used are finely divided copper (copper bronze), copper(I) oxide, copper(II) oxide, copper(II) sulphate, copper(I) chloride or copper acetate.

8. Process for the preparation of 1,4-diamino-anthraquinone-2-sulphonic acid and its salts, according to claim 1, characterised in that the copper catalyst used is copper(II) sulphate.

* * * * *

UNITED STATES PATENT AND TRADEMARK OFFICE
CERTIFICATE OF CORRECTION

PATENT NO. : 4,521,341
DATED : June 4, 1985
INVENTOR(S) : Friedrich W. Kröck, et al It is certified that error appears in the above-identified patent and that said Letters Patent is hereby corrected as shown below:

Page 1, under "Inventors", line 2 — Delete "Neoff" and substitute --Neeff--

Col. 2, line 24 — Correct spelling of "bromo-anthraquinone"

Col. 5, line 16 — After "anthraquinone-" delete "b"

Signed and Sealed this

Fifteenth Day of October 1985

[SEAL]

Attest:

Attesting Officer

DONALD J. QUIGG

*Commissioner of Patents and Trademarks—Designate*